United States Patent [19]

Schmitt et al.

[11] 4,376,835
[45] Mar. 15, 1983

[54] CALCIUM DEPLETED ALUMINUM FLUOROSILICATE GLASS POWDER FOR USE IN DENTAL OR BONE CEMENTS

[75] Inventors: Werner Schmitt; Robert Purrmann, both of Starnberg; Peter Jochum, Hechendorf; Oswald Gasser, Seefeld, all of Fed. Rep. of Germany

[73] Assignee: ESPE Fabrik Pharmazeutischer Praparate GmbH, Seefeld, Fed. Rep. of Germany

[21] Appl. No.: 336,850

[22] Filed: Jan. 4, 1982

Related U.S. Application Data

[63] Continuation of Ser. No. 164,322, Jun. 30, 1980, abandoned.

[30] Foreign Application Priority Data

Jul. 18, 1979 [DE] Fed. Rep. of Germany ....... 2929121

[51] Int. Cl.$^3$ .................. A61F 1/00; B32B 17/00; B32B 17/06; C08L 33/02
[52] U.S. Cl. ........................... 523/116; 65/31; 106/35; 156/663; 260/998.11; 428/375; 428/406; 428/428; 433/228; 501/39; 501/57; 501/63; 501/73
[58] Field of Search .................. 428/406, 375; 65/31; 433/228; 156/663; 427/309; 106/35; 3/1.9; 501/39, 57, 63, 73; 523/116; 525/362; 260/998.11

[56] References Cited

U.S. PATENT DOCUMENTS

| | | | |
|---|---|---|---|
| 3,814,717 | 6/1974 | Wilson et al. | 106/35 X |
| 3,986,998 | 10/1976 | Schmitt et al. | 106/35 X |
| 4,063,001 | 12/1977 | Zlochower | 156/663 X |
| 4,209,434 | 6/1980 | Wilson et al. | 106/35 X |
| 4,215,033 | 7/1980 | Bowen | 501/35 X |
| 4,271,057 | 6/1981 | Drake et al. | 501/57 X |

OTHER PUBLICATIONS

Wilson, A. D., "Alumino-Silicate Polyacrylic Acid and Related Cements" Br. Polym. J., May, 1974, 6 pp. 165–179.

*Primary Examiner*—Helen M. McCarthy
*Attorney, Agent, or Firm*—Daley, Boettcher & Brandt

[57] ABSTRACT

A calcium aluminum fluorosilicate glass powder is disclosed which has average particle size of at least 0.5 microns, and is characterized in that the calcium in the surface of the powder's particles is depleted so that the quotient of the atomic ratio Si/Ca at the surface of the particles and the atomic ratio Si/Ca in the core region of the particles is at least 2.0, more preferably at least 3.0 and most preferably at least 4.0. The glass powder may be prepared by surface treating calcium aluminum fluorosilicate glass powder particles with an acid which forms calcium salts, washing the calcium salts off the treated particles and drying the washed particles.

The glass powder has utility in self-hardening glass ionomer cements, such as dental or bone cements. Cements formed from the glass powder exhibit reduced periods of water sensitivity, while permitting sufficient time for processing.

30 Claims, 1 Drawing Figure

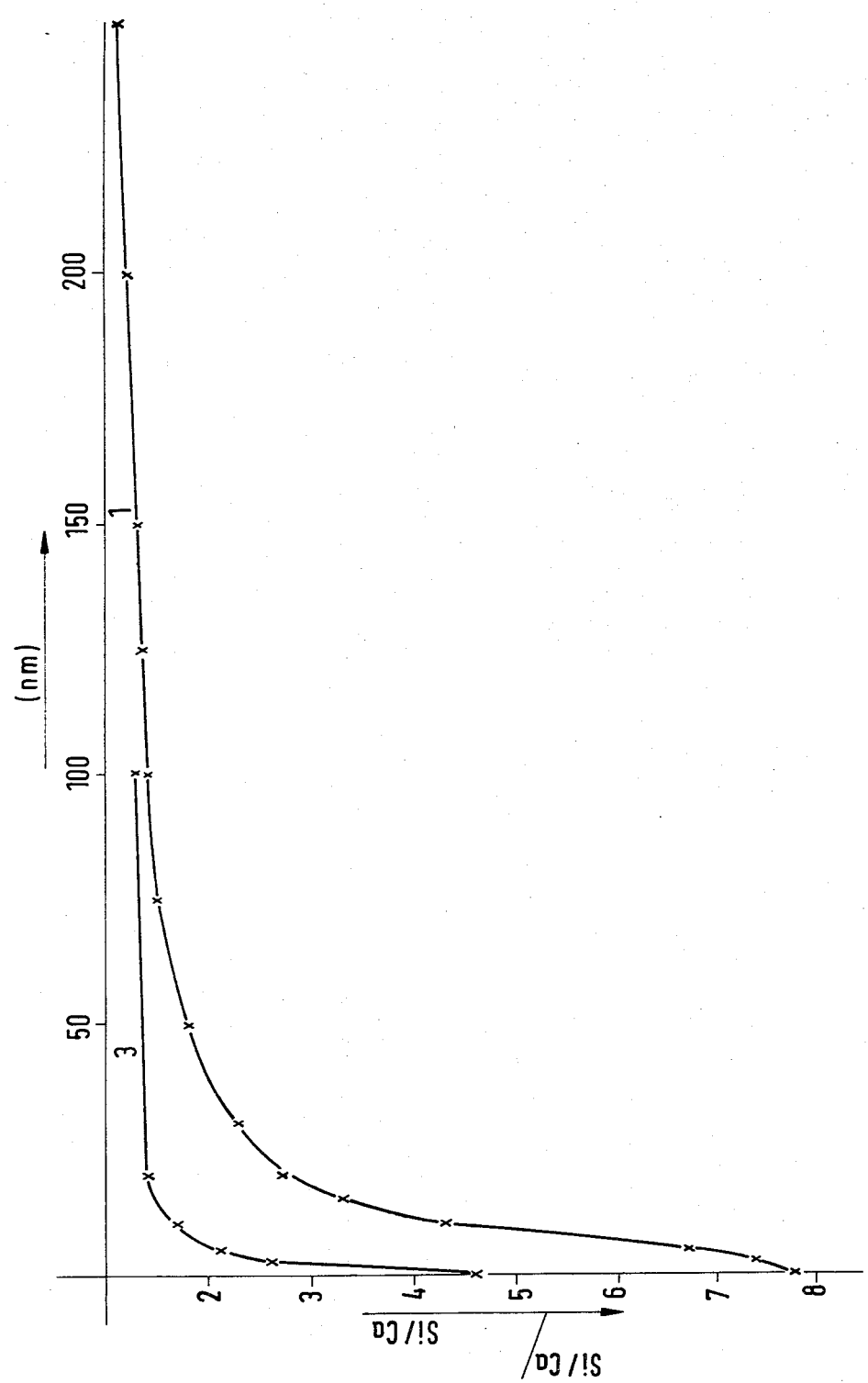

CALCIUM DEPLETED ALUMINUM FLUOROSILICATE GLASS POWDER FOR USE IN DENTAL OR BONE CEMENTS

This application is a continuation of application Ser. No. 164,322, filed June 30, 1980, now abandoned.

BRIEF SUMMARY OF THE INVENTION

This invention provides a calcium aluminum fluorosilicate glass powder the particles of which have an average size of at least 0.5 microns, characterized in that the powder particles are so depleted of calcium at the surface that the quotient of the atomic ratio Si/Ca at the surface of the powder particles and the atomic ratio Si/Ca in the core region is at least 2.0 The powder may be prepared by (a) treating a calcium aluminum fluorosilicate glass powder the particles of which have an average size of at least 0.5 microns and a maximum particle size of 150 microns with an aqueous acid solution having a concentration of 0.01 to 10% by weight;

(b) separating the treated powder from the acid solution;

(c) washing calcium salts from the surface of the separated powder; and (d) drying the washed powder. The powder may be employed in self-hardening glass ionomer cements having utility as bone or dental cements.

BACKGROUND OF THE INVENTION

The invention relates to glass powders that may be employed in cements useful in medicine or dentistry, e.g., in bone or dental cements, especially in the so-called glass ionomer cement.

Glass ionomer cements have been described in German patent application (OS) No. 2,061,513. They consist of a calcium aluminum fluorosilicate glass powder and a mixing fluid which may generally be designated as an aqueous solution of a polycarboxylic acid. The resulting composition may be employed, for example, as a permanent filling material in dentistry. Its significance resides in the fact that it is the first tooth filling material that is satisfactory in cosmetic and mechanical respect and that is simultaneously physiologically so unobjectionable that it may be directly filled into the tooth without any underfilling and similar measures.

A disadvantage of the glass ionomer cements resides in their high water sensitivity during and after the setting reaction. While during the setting reaction the water sensitivity is hardly avoidable for principal reasons, the water resistance of the compositions after setting can be improved in two ways, namely by the use of a highly reactive powder composition or by the use of an especially reactive setting fluid. Especially favorable results are naturally obtained by the combination of the two possibilities. However, in that case the reaction is so rapid that the processing period, i.e., the period of time available for introducing the cement into the cavity and modelling it therein, is extremely short. In many cases hardening takes place already during mixing. In order to ensure sufficiently long processing time, less reactive powders and less reactive fluids are employed, so that the preparations presently available on the market are all water-sensitive for a longer period of time.

From German Pat. No. 1,267,589, it has been known to treat glass grit used in the production of porous sintered structures (filters) with bases or acids in order to cleave the surface of the glass particles.

It is an object of the invention to reduce the water sensitivity of cements useful in medicine and dentistry and based on glass powders and polycarboxylic acids while at the same time ensuring a sufficiently long processing period.

It has now been found that this object is realized when the powder component of the glass ionomer cements is a calcium aluminum fluorosilicate glass whose powder particles are on their surfaces depleted of calcium ions as compared with the average composition thereof.

Therefore, the subject matter of the invention is the calcium aluminum fluorosilicate glass powder described in the patent claims and its use.

DETAILED DESCRIPTION OF THE INVENTION

The calcium aluminum fluorosilicate glass powders of the invention preferably consist of:

| Component | Calculated As | Percent By Weight |
|---|---|---|
| Si | $SiO_2$ | 20–60 |
| Al | $Al_2O_3$ | 10–50 |
| Ca | CaO | 1–40 |
| F | F | 1–40 |
| Na | $Na_2O$ | 0–10 |
| P | $P_2O_5$ | 0–10 | besides oxygen, in the core region of the powder particles, and altogether 0 to 20% by weight, calculated as oxides, of B, Bi, Zn, Mg, Sn, Ti, Zr, La or other trivalent lanthanoids, K, W, Ge, as well as further additives which do not adversely affect the properties and which are physiologically unobjectionable.

Preferably the core region of the powder particles consists of:

| Si | as | $SiO_2$ | 25–50% by weight |
| Al | as | $Al_2O_3$ | 10–40% by weight |
| Ca | as | CaO | 10–35% by weight |
| F | | | 5–30% by weight |
| Na | as | $Na_2O$ | 0–8% by weight |
| P | as | $P_2O_5$ | 1–10% by weight | and 0 to 10% by weight of $B_2O_3$, $Bi_2O_3$, ZnO, MgO, $SnO_2$, $TiO_2$, $ZrO_2$, $La_2O_3$ or other oxides of trivalent lanthanoids, $K_2O$, $WO_3$, $GeO_2$ and further additives which do not adversely affect the properties and which are physiologically unobjectionable.

Especially preferred components are:

| Si | as | $SiO_2$ | 25–45% by weight |
| Al | as | $Al_2O_3$ | 20–40% by weight |
| Ca | as | CaO | 10–30% by weight |
| F | | | 10–30% by weight |
| Na | as | $Na_2O$ | 1–8% by weight |
| P | as | $P_2O_5$ | 1–10% by weight |

Regarding the empirical chemical composition in the core region of the powder particles, glasses may be used which have been described for example in German Patent Applications (OS) No. 2,061,513 or (AS) No. 2,065,824.

Examples of preferred compositions in the core region are listed in the following Table I:

TABLE I

EXAMPLES FOR THE CORE REGION COMPOSITION
OF GLASS POWDERS OF THE INVENTION

| Percent By Weight | A | B | C | D |
|---|---|---|---|---|
| Si as $SiO_2$ | 35.0 | 27.6 | 29.0 | 45.4 |
| Al as $Al_2O_3$ | 30.4 | 26.0 | 25.1 | 35.0 |
| Ca as CaO | 14.9 | 28.8 | 24.6 | 10.1 |
| F | 17.7 | 17.0 | 23.0 | 10.4 |
| Na as $Na_2O$ | 2.7 | 2.1 | 2.2 | 6.9 |
| P as $P_2O_5$ | 6.9 | 8.3 | 5.8 | 2.4 |

The glass powder particles of the invention are depleted of calcium at their surface such that the quotient of the atomic ratio Si/Ca at the surface of the powder particles and the atomic ratio Si/Ca in the core region is at least 2,0, preferably at least 3.0, and most preferably at least 4.0. The calcium content of the powder particles of the invention increases asymptotically from the surface to the core region.

The depth of the depletion zone depends on the conditions given in each individual case, especially on the desired processing period of the cements prepared from the glass powders of the invention. In practice it is favorable when the calcium depletion extends at least so deeply that the processing period of the mixture of the powders of the invention and the polycarboxylic acid solution is at least 1.5 min. at 23° C. In general, the depletion zone preferably extends at least to a depth of about 10 nm, more preferably to at least about 20 nm, and most preferably to at least about 100 nm. These ranges are particularly suited for use of the glass powders of the invention in dentistry. For other purposes, e.g., for use in bone cements, the depletion zone may also be deeper and may be 200 to 300 nm, for example.

As will be explained further below, the glass powders of the invention are produced by surface treatment of glass powders having a composition corresponding to the core region of the powders of the invention. Upon surface treatment the number of silicon atoms per unit volume remains substantially constant. The actual change in the absolute number of atoms per unit volume of other types of atoms is therefore obtained by forming the quotient of the relative atom proportion with the percentage silicon proportion, as is shown later by means of a practical example. The quotient of the atomic ratio Si/Ca at the surface of the powder particles and the atomic ratio Si/Ca in the core region therefore constitutes a useful value to characterize the glass powders of the invention. The accompanying figure of drawing represents a plot of the quotient of the atomic ratio Si/Ca at the point of measurement and the atomic ratio Si/Ca in the core region against the depth of the measurement for powders of the invention as described in Examples 1 and 3. The examples and FIG. 1 demonstrate that the atomic ratio Si/Ca for the individual layers of the glass powder asymptotically approaches the value of untreated starting material and thus of the core region of the treated powder.

The surface measurement to determine Ca depletion of the glass powders of the invention is suitably carried out by photo electron spectroscopy for chemical analysis (ESCA). This method has been described by R. S. Swingle II and W. M. Riggs in Critical Reviews in Analytical Chemistry, Vol. 5, Issue 3, pages 267 to 321, 1975 and by K. Levsen in "Chemie in unserer Zeit", Vol. 40, pages 48 to 53, 1976.

The measuring data underlying the present description were determined under the following measuring conditions of ESCA measurement:

| Apparatus: | Scanning Auger ESCA spectrometer, Model PHI550, of Messrs. Physical Electronics Industries, Munich (cf. Perkin-Elmer brochure ESCA/SAM, PHI Data Sheet 1052 2-79 3m) |
|---|---|
| Excitation: | 400 watt Mg radiation |
| Grid penetration energy: | 100 eV |
| Time Constant: | 0.1 sec. |

The glass powders of the invention have an average particle size (weight average) of at least 0.5 microns, preferably at least 1 micron, and most preferably at least 3 microns. For dental purposes the average particle size (weight average) is 1 to 20 microns, preferably 3 to 15 microns, most preferably 3 to 10 microns. The particles have a maximum particle size of 150 microns, preferably 100 microns, especially 60 microns. For use as dental bonding cement the maximum particle size is 25 microns, preferably 20 microns. In order to achieve good mechanical properties a not excessively narrow particle size distribution is favorable, as usual, which is achieved, for example, by conventional grinding and classifying of the coarse.

The glass powders of the invention are prepared from glass powders having the average composition of the core region of the powders of the invention. To this end the glass powders described, for example, in German (OS) No. 2,061,513 and in Table I are suitable. The glass powders employed as starting materials are obtained as usual by fusing the starting components together at temperatures above 950° C., quenching, and grinding. The starting components may be, for example, the compounds stated in German (OS) No. 2,061,513 in suitable quantitative ranges.

The thus obtained powders are then subjected to a surface treatment. The powders of the invention are obtainable, for example, by removal of Ca by suitable chemical agents.

According to one embodiment of the invention the starting glass powders are treated on the surface with acid, preferably at room temperature. To this end substances containing acidic groups are employed, preferably substances forming soluble calcium salts. Sparing water-solubility of the respective calcium salts may be compensated to a certain degree by a large amount of liquid per unit of powder. The reaction period varies between a few minutes and several days, depending on the strength and concentration of the acid employed.

Thus, for instance, for the preparation of the powders hydrochloric, sulfuric, nitric, acetic, propionic and perchloric acid may be used.

The acids are employed at a concentration of 0.01 to 10% by weight, preferably from 0.05 to 3% by weight.

After the respective reaction period the powders are separated from the solution and thoroughly washed to leave substantially no soluble calcium salts on the surface of the powder particles. Finally the powder is dried, preferably above 70° C., and screened to the desired particle size ranges.

The stronger the acid employed and the longer a given acid acts on the powder the longer will be the processing period after mixing with the mixing fluid.

The favorable surface character of the powders of the invention permits the use of an especially high powder/fluid ratio in the cement mix resulting in high strength values of the hardened material. The possibility of using a particularly reactive mixing fluid has the same effect. Furthermore, the processing period of a cement of the invention may be tailored to meet the user's requirements. The length of the processing period hardly influences the subsequent hardening period, so that also upon long processing periods rapid setting and early water insensitivity occurs.

The glass powders of the invention are thus especially well suited for use in dental and bone cements. Therefore, the invention also relates to the use of the glass powders of the invention for the preparation of self-hardening glass ionomer cements.

The powders of the invention may be mixed, to form dental cements or bone cements, with the conventional aqueous polycarboxylic acid solutions as described, for example, in German patent applications (OS) No. 2,061,513, (OS) No. 2,439,882, and (OS) No. 2,101,889. Suitable polycarboxylic acids are polymaleic acid, polyacrylic acid and mixtures thereof, or copolymers, especially maleic acid/acrylic acid copolymers and/or acrylic acid/itaconic acid copolymers. It is self-evident that with the use of an extremely reactive glass powder a less reactive polycarboxylic acid will be employed in order to obtain a satisfactory hardening characteristic.

In order to accelerate and improve hardening of said glass ionomer cements chelating agents may be added during mixing, in a manner known per se from German patent application (OS) No. 2,319,715. Preferably tartaric acid, in the usual concentrations, is added as chelating agent to the mixing fluid.

Instead of the customary use of the glass powders of the invention, namely with the aqueous polycarboxylic acid solution as mixing fluid, the glass powder may also be pre-mixed in the corresponding ratio with the dry powdered polycarboxylic acid, as the solid substances do not undergo reaction with each other. In that case water is used as mixing fluid, preferably an aqueous solution of a chelating agent, especially tartaric acid, together with conventional additives such as bacteriostatic agents, if appropriate.

In order to avoid metering errors and to attain optimum mechanical properties, the use of the powders of the invention in pre-dosaged form is advantageous. In one embodiment the glass powder is metered out in plastic containers. Then the cement can either be mixed mechanically within said plastic capsules, or the container may be emptied and the mix prepared by hand. The aqueous polycarboxylic acid solution in such a case is metered, for example, with a dripping bottle or with a syringe. The use of the powder of the invention in so-called shaker capsules, e.g., corresponding to German patent application (OS) No. 2,324,296, is especially suitable. A predetermined quantity of powder is held in readiness in a so-called main compartment, while the fluid is contained in a separate cushion beneath a lateral clip. By exerting pressure on said clip the fluid is sprayed through a bore into the main compartment and is then available for mechanical mixing. In both types of capsules the pure glass powder may be replaced by a mixture of glass powder and dry polycarboxylic acid in predetermined quantitites. The fluid component is then water or an aqueous solution of a chelating agent, especially tartaric acid.

The use of the mixture of glass powder of the invention and dry polycarboxylic acid is especially advantageous if said mixture is pelletized. To this end the dry polycarboxylic acid is used in finely divided form after removal of coarse portions. After thorough blending of said polycarboxylic acid powder with the glass powder of the invention pellets may be made in a conventional pelletizing machine. The compacting pressure must be selected such that after the addition of the mixing fluid (water or aqueous tartaric acid solution, for example), the pellets can still be readily worked into a cement while, on the other hand, they possess sufficient mechanical stability for transportation. Pellets made in this way permit especially simple mixing into a cement paste after brief dissolution, e.g., in the corresponding amount of tartaric acid solution. The mixing fluid may be added, for example, from a drip bottle or from a syringe.

The following examples serve to explain the invention:

EXAMPLE 1

According to methods known per se (e.g., OS No. 2,061,513) a glass powder is prepared consisting of:

| | |
|---|---|
| Si as $SiO_2$ | 35.0% by weight |
| Al as $Al_2O_3$ | 30.4% by weight |
| Ca as CaO | 14.9% by weight |
| Na as $Na_2O$ | 2.7% by weight |
| P as $P_2O_5$ | 6.9% by weight |
| F | 17.7% by weight |

A finely particulate glass powder is obtained by grinding the quenched glass composition in a ball mill.

100 grams of said powder are slurried in 1000 grams of 0.15% aqueous HCl solution and stirred vigorously for 1 hour. Thereafter the slurry is filtered, washed free from chloride, dried for 2 hours at 120° C. and screened to a particle size of less than 60 microns. The powder then has a weight average particle size of about 8 microns.

From the following Table II the results of ESCA measurements of the atomic composition of the sample treated according to the invention in various depths are apparent:

TABLE II

| | Atomic Percent (standardized to $\Sigma = 100\%$) | | | | | | |
|---|---|---|---|---|---|---|---|
| | Si/Ca | O | Si | Al | Ca | F | P |
| Surface | 18.0 | 53.7 | 27.0 | 11.8 | 1.5 | 2.4 | 3.5 |
| 2.5 nm | 16.9 | 51.5 | 27.0 | 13.7 | 1.6 | 3.2 | 3.1 |
| 5 nm | 15.4 | 50.0 | 27.8 | 14.1 | 1.8 | 3.5 | 2.7 |
| 10 nm | 9.8 | 49.0 | 25.5 | 15.8 | 2.6 | 5.0 | 2.1 |
| 15 nm | 7.6 | 47.6 | 24.4 | 16.5 | 3.2 | 6.2 | 2.0 |
| 20 nm | 6.2 | 47.0 | 23.7 | 16.8 | 3.8 | 7.0 | 1.7 |
| 30 nm | 5.2 | 47.2 | 22.5 | 16.9 | 4.3 | 7.5 | 1.5 |
| 50 nm | 4.2 | 45.8 | 20.9 | 18.7 | 5.0 | 8.4 | 1.2 |
| 75 nm | 3.5 | 44.5 | 19.8 | 19.9 | 5.7 | 10.0 | 1.0 |
| 100 nm | 3.2 | 44.0 | 19.6 | 18.9 | 6.2 | 10.1 | 1.1 |
| 125 nm | 3.1 | 42.4 | 19.9 | 20.2 | 6.4 | 10.0 | 1.1 |
| 150 nm | 2.9 | 41.9 | 19.3 | 20.6 | 6.6 | 10.5 | 1.0 |
| 200 nm | 2.8 | 41.8 | 19.0 | 21.0 | 6.9 | 10.7 | 0.7 |
| 250 nm | 2.5 | 41.2 | 18.4 | 20.9 | 7.3 | 11.3 | 0.9 |

From the table and the attached figure it is apparent that the Si/Ca ration from the surface to the center of the particles approaches asymptotically a limit in the core region of about 2.3. The quotient of the Si/Ca atomic ratio at the surface and that in the core region therefore is about 7.8 in this example.

EXAMPLE 2

The powder used in Example 1 is treated in the manner described in Example 1 except that in lieu of hydrochloric acid, the acids listed in the table are used with the corresponding stirring periods.

| Acid | Acid Concentration | Stirring Period |
| --- | --- | --- |
| Sulfuric acid | 0.5% | 1 hour |
| Acetic acid | 0.3% | 20 hours |
| Nitric acid | 0.5% | 1 hour |
| Acetic acid | 3.0% | 1 hour |
| Propionic acid | 2.0% | 1 hour |
| Perchloric acid | 0.3% | 1 hour |

In each instance glass powders are obtained which correspond approximately to that of Example 1.

EXAMPLE 3

10 grams of a commercially available glass ionomer cement powder of the composition of Table I C (De Trey, Aspa, A. D. International, London, England, weight average of particle size about 6.5 microns) are treated with 100 grams of 0.4% aqueous hydrochloric acid solution as described in Example 1.

The atomic composition of this powder was determined in various depths according to the ESCA method. The results are compiled in the following Table III:

TABLE III

| | Atomic Percent (standardized to Σ = 100%) | | | | | | |
| --- | --- | --- | --- | --- | --- | --- | --- |
| | Si/Ca | O | Si | Al | Ca | F | P |
| Surface | 3.2 | 51.0 | 16.9 | 12.0 | 5.3 | 7.8 | 7.0 |
| 2.5 nm | 1.8 | 43.1 | 16.2 | 12.6 | 8.8 | 13.4 | 5.9 |
| 5 nm | 1.5 | 40.5 | 15.9 | 12.5 | 10.5 | 15.7 | 4.9 |
| 10 nm | 1.2 | 37.4 | 15.1 | 11.6 | 12.6 | 19.1 | 4.2 |
| 20 nm | 1.0 | 34.3 | 14.4 | 11.8 | 14.6 | 21.6 | 3.2 |
| 100 nm | 0.9 | 32.1 | 15.0 | 12.1 | 16.4 | 23.1 | 1.4 |

From the table and the attached figure, it is apparent that the Si/Ca ratio from the surface to the particle center asymptotically approaches a limit in the core region of 0.7. The quotient of the atomic ratio Si/Ca at the surface and that of the core region therefore is 4.6.

EXAMPLE 4

The untreated powder of the prior art used in Example 1 and the powder of the invention according to Example 1 are each passed through a screen having sieve openings of a size of 60 microns. The powders are mixed with commercially available mixing fluid for glass ionomer cements (acrylic acid/itaconic acid copolymer, De Trey, Aspa Fluid, A. C. International, London, England) at a weight ratio of 3.5:1. Hardening is thereafter observed on a rheometer at 28° C.

| | |
| --- | --- |
| Untreated glass powder According to Example 1 (prior art) | Processing period: Setting commences immediately |
| Treated powder According to Example 1 (invention) | Processing period: 3 min 30 sec. Setting period: 6 min 10 sec. |

EXAMPLE 5

The powder of the invention prepared according to Example 1 is mixed to form a paste with about a 45% aqueous polymaleic acid solution (according to OS 2,101,889) at a weight ratio of 3.5:1. Previously 10% by weight of tartaric acid had been added to the polymaleic acid solution. Setting of the cement mix was observed on a rheometer:

| | |
| --- | --- |
| Processing period: | 2 minutes |
| Setting period: | 4 minutes. |

The mix provides a favorable processing period whereafter it sets rapidly.

EXAMPLE 6

The water sensitivity of the glass ionomer cements is determined according to the following method:

Cylindrical shaped structures of 10 mm diameter and 2.5 mm height are filled with the freshly mixed material under test and are placed into a solution of 1% patent blue in water (room temperature) 10 minutes after mixing. The shaped structures are left in the solution for 10 minutes, then rinsed and dried. The shaped article is sanded flat with fine sand paper to about ⅓ on the round side.

The thickness of the dye layer penetrated into the structure is measured under the microscope. Five measured values are determined haphazardly and therefrom the average is formed.

| Powder | Fluid | Powder/ Fluid Ratio | Dye Penetration Depth (microns) |
| --- | --- | --- | --- |
| Example 1 (invention) | aqueous solution of acrylic/itaconic acid copolymer (commercial: De Trey "Aspa") | 3.5 | 0 |
| Tab I C (commercial: De Trey, "Aspa") | aqueous solution of acrylic/itaconic acid copolymer (commercial: De Trey "Aspa") | 3.0 (according to manufacturer's prescription) | 125 |
| Example 1 (invention) | commercial (G.C. "Fuji") | 3.5 | 0 |
| Tab I D (commercial: G.C. "Fuji") | commercial (G.C. "Fuji") | 2.3 (according to manufacturer's prescription) | 65 |

EXAMPLE 7

The powder prepared according to Example 1, after the addition of suitable pigments in the conventional quantities, gives a powder which is suited as cement mix in the replacement of defective tooth portions. About 45% polymaleic acid solution (according to OS 2,101,889) to which 10% tartaric acid were added is used as mixing fluid.

After mixing said powder and the fluid at a weight ratio of 3.5:1 a paste of good consistency is obtained which, after setting, gives a cement of tooth-like transparency having the following physical data:

| | |
| --- | --- |
| Compressive strength | 175 MPa |
| Surface hardness: | 400 MPa |

| | |
|---|---|
| Processing period: | 2 minutes |
| Setting period: | 4 minutes |
| Water penetration depth: (according to Example 6) | 0 micron |

EXAMPLE 8

A glass powder is prepared according to methods known per se (e.g., German OS No. 2,061,513) having the following composition:

| | |
|---|---|
| Si as $SiO_2$ | 27.6% by weight |
| Al as $Al_2O_3$ | 26.0% by weight |
| Ca as CaO | 28.8% by weight |
| Na as $Na_2O$ | 2.1% by weight |
| P as $P_2O_5$ | 8.3% by weight |
| F | 17.0% by weight |

A finely particulate glass powder is obtained by grinding the quenched glass composition in a ball mill.

The resulting powder is treated with 0.1% aqueous hydrochloric acid solution for 1 hour as described in Example 1. Thereafter it is passed through a screen with 20 microns sieve openings. The resulting powder is suited for use as bonding cement for artificial teeth.

To this end the resulting powder is mixed at a weight ratio of 1.8:1 with a commercial mixing fluid for glass ionomer bonding cements (Chem. Bond, A. C. International, London, England). The low viscosity mixture remains processable for about 3 minutes at room temperature and has set after 8 minutes.

EXAMPLE 8

100 grams of the powder of the invention described in Example 7 are mixed with 10.5 grams of a dry polymaleic acid powder (less than 60 microns) (prepared, for example, according to OS No. 2,101,889). From the homogeneous mixture pellets of about 200 mg (8 mm diameter, about 2 mm thickness) are produced in the conventional manner.

One of said pellets is briefly softened in 34 mg of 14% tartaric acid solution. After stirring with light pressure one obtains a homogeneous paste of good consistency which is useful as self-hardening tooth cement.

EXAMPLE 10

The powder of the invention described in Example 7 is metered in portions of 280 mg each into the mixing compartment of shaker capsules as described in German (OS) No. 1,910,885. Said capsule contains as a separate compartment a cushion of plastic-coated aluminum filled with 96 mg of an about 45% aqueous polymaleic acid solution. When using the thus prepared capsule as described in the above-mentioned (OS) and mixing the components with a mechanical mixer one obtains a cement suited as permanent filling material for tooth cavities.

EXAMPLE 11

A mixture of 285 mg of a powder of the invention corresponding to Example 7 and 35 mg of a dried maleic acid polymer is filled into the mixing compartment of a shaker capsule according to German (OS) No. 1,910,885. Said capsule contains as a separate compartment a cushion of plastic-coated aluminum filled with 54 mg of a 14% tartaric acid solution. Following the procedure described in Example 10 one obtains again a cement suited as permanent dental filling material.

EXAMPLE 12

100 grams of the powder used in Example 1 are intensively stirred with 1000 grams of 3% aqueous acetic acid solution for 2 hours. Thereafter the slurry is filtered, thoroughly washed, dried for 2 hours at 120° C. and screened to a particle size of less than 60 microns.

After mixing with about 45% polymaleic acid solution in a weight ratio of 2.5:1 a cement composition is obtained which remains processable for about 5 minutes and which has set after 8 minutes.

This cement composition is especially well suited as bone cement, e.g., for bonding artificial hip joints.

What is claimed is:

1. A calcium aluminum fluorosilicate glass powder reactable with a mixing fluid to form a self hardening glass ionomer cement exhibiting properties of reduced period of water sensitivity and at the same time insuring a sufficiently long processing period, said glass powder being characterized by particles having an average size of at least 0.5 microns, and in that the level of calcium present at the surface of the powder particles is depleted relative to the level of the calcium present in the core region and to the extent that the quotient of the atomic ratio Si/Ca at the surface of the powder particles and the atomic ratio Si/Ca in the core region is at least 2.0, with the calcium content increasing asymptotically from the surface to the core region.

2. The glass powder of claim 1 having a core region comprising:
   20–60 weight percent $SiO_2$,
   10–50 weight percent $Al_2O_3$,
   1–40 weight percent CaO,
   1–40 weight percent F,
   0–10 weight percent $Na_2O$, and
   0–10 weight percent $P_2O_5$.

3. The glass powder of claim 2 further comprising 0–20% by weight of an oxide of the group consisting of B, Bi, Zn, Mg, Sn, Ti, Zr, La, a trivalent lanthanide, K, W and Ge.

4. The glass powder of claim 3 wherein the oxides are selected from the group consisting of $B_2O_3$, $Bi_2O_3$, ZnO, MgO, $SnO_2$, $TiO_2$, $ZrO_2$, $La_2O_3$, $K_2O$, $WO_3$ and $GeO_2$.

5. The glass powder of claim 2 having a core region comprising:
   25–50 weight percent $SiO_2$,
   10–40 weight percent $Al_2O_3$,
   10–35 weight percent CaO,
   5–30 weight percent F,
   0–8 weight percent $Na_2O$, and
   1–10 weight percent $P_2O_5$.

6. The glass powder of claim 5 further comprising 0–10 weight percent of an oxide of the group consisting of B, Bi, Zn, Mg, Sn, Ti, Zr, La, a trivalent lanthanide, K, W and Ge.

7. The glass powder of claim 2 having a core region comprising:
   25–45 weight percent $SiO_2$,
   20–40 weight percent $Al_2O_3$,
   10–30 weight percent CaO,
   10–30 weight percent F,
   1–8 weight percent $Na_2O$, and
   1–10 weight percent $P_2O_5$.

8. The glass powder of claim 1 wherein the quotient is at least 3.0.

9. The glass powder of claim 1 wherein the quotient is at least 4.0.

10. The glass powder of claim 1 wherein the surface calcium depletion extends to a depth of at least about 10 nm.

11. The glass powder of claim 10 wherein the depletion extends to a depth of at least 20 nm.

12. The glass powder of claim 10 wherein the depletion extends to a depth of at least 100 nm.

13. The glass powder of claim 10 wherein the depletion extends to a depth of about 200–300 nm.

14. The glass powder of claim 1 wherein the average particle size is at least 1 micron.

15. The glass powder of claim 1 wherein the average particle size is at least 3 microns.

16. The glass powder of claim 1 wherein the maximum particle size is 150 microns.

17. The glass powder of claim 1 wherein the maximum particle size is 100 microns.

18. A self-hardening glass ionomer cement comprising an aqueous mixture of the calcium aluminum fluorosilicate glass powder of claim 1 having a maximum particle size of 150 microns, a polycarboxylic acid and chelating agent.

19. The cement of claim 18 wherein the average particle size of the powder is 1–20 microns and the maximum particle size is 100 microns.

20. The cement of claim 19 wherein the average particle size of the powder is 3–10 microns and the maximum particle size is 60 microns.

21. The cement of claim 18 wherein the maximum particle size is 25 microns.

22. The cement of claim 18 wherein the maximum particle size is 20 microns.

23. A dental filling material comprising the cement of claim 18.

24. A dental filling material comprising the cement of claim 19.

25. A dental filling material comprising the cement of claim 20.

26. A dental filling material comprising the cement of claim 21.

27. A dental filling material comprising the cement of claim 22.

28. A dental bonding cement comprising the cement of claim 21.

29. A bone cement comprising the cement of claim 18.

30. A dental bonding cement comprising the cement of claim 22.

* * * * *

UNITED STATES PATENT AND TRADEMARK OFFICE
CERTIFICATE OF CORRECTION

PATENT NO. : 4,376,835
DATED : March 15, 1983
INVENTOR(S) : Werner Schmitt et al.

It is certified that error appears in the above-identified patent and that said Letters Patent are hereby corrected as shown below:

In the Drawing:

the abscissa legend should read --

$Si/Ca$ $Si/Ca$- in core region   -- the ordinate legend should read --

Depth (nm)   -- the "3" and "1" identifying the respective curves should read

-- Example 3 -- and

-- Example 1 -- , respectively

Signed and Sealed this

Twelfth Day of February 1985

[SEAL]

Attest:

DONALD J. QUIGG

Attesting Officer   Acting Commissioner of Patents and Trademarks